United States Patent [19]

Lattin et al.

[11] Patent Number: 4,457,748
[45] Date of Patent: Jul. 3, 1984

[54] NON-INVASIVE DIAGNOSIS METHOD
[75] Inventors: Gary A. Lattin, Forest Lake; Richard P. Spevar, Moundsview, both of Minn.
[73] Assignee: Medtronic, Inc., Minneapolis, Minn.
[21] Appl. No.: 338,365
[22] Filed: Jan. 11, 1982
[51] Int. Cl.$^3$ .............................................. A61N 1/30
[52] U.S. Cl. .................. 604/20; 128/419 R; 128/760
[58] Field of Search .................. 128/743, 760, 419 R; 604/20, 289–290, 304, 307, 355

[56] References Cited

U.S. PATENT DOCUMENTS

| | | | |
|---|---|---|---|
| 2,784,715 | 3/1957 | Kestler | 604/20 |
| 3,043,669 | 7/1962 | Charles | 422/58 X |
| 3,447,904 | 6/1969 | Rupe | 436/125 |
| 3,492,216 | 1/1970 | Riseman et al. | 204/419 |
| 3,699,963 | 10/1972 | Zaffaroni | 604/897 |
| 3,703,890 | 11/1972 | Saunders, Jr. | 604/307 X |
| 3,794,910 | 2/1974 | Ninke et al. | 128/760 X |
| 3,894,531 | 7/1975 | Saunders, Jr. | 604/307 X |
| 4,141,359 | 2/1979 | Jacobsen et al. | 604/20 |
| 4,163,039 | 7/1979 | Emrich | 436/79 X |
| 4,190,060 | 2/1980 | Greenleaf et al. | 128/760 |
| 4,209,020 | 6/1980 | Nielsen | 128/640 |
| 4,230,105 | 10/1980 | Harwood | 128/156 |
| 4,250,878 | 2/1981 | Jacobsen et al. | 604/20 |
| 4,325,367 | 4/1982 | Tapper | 128/803 X |
| 4,329,999 | 5/1982 | Phillips | 128/760 |

FOREIGN PATENT DOCUMENTS 1965195 7/1971 Fed. Rep. of Germany ...... 128/640

OTHER PUBLICATIONS

"Evaluation of the 3M Patch Test for Cystic Fibrosis", Papers, 1967.
Knights, Jr. et al., "Simplified Screening Test for Cystic Fibrosis of the Pancreas.", J.A.M.A., vol. 169, No. 12, 3/21/59, pp. 80–90.
Gluck, L., "A Patch Test for Chloride in Sweat as a Simple Screening Method for Detecting Cystic Fibrosis of the Pancreas." Pediatrics, Apr. 1959, pp. 731–737.
Brochure Entitled "Quantab TM Chloride Titrators." Oct. 4, 1979.
"Iontophoresis-A Major Advancement", The Eye, Ear, Nose and Throat Monthly, vol. 55, Feb. 1976.
"Painless Anesthesia", Medical Electronics, by Yvonne Baskin, University of Utah.
"Iontophoresis Local Anesthesia for Conjunctival Surgery", Annals of Opthamology, May 1978.
"Treatment of Orthopaedic Infections with Electrically Generated Silver Ions", The Journal of Bone and Joint Surgery, vol. 60-A, No.7, Oct. 1978.
"Opinions and Comments", Physical Therapy, vol. 57, No. 10, Oct. 1977, pp. 1193–1194.
"Suggestion from the Field", Re: Acetic Acid Iontophoresis for Calcium Deposits, Physical Therapy, vol. 57, No. 6, Jun. 1977, pp. 658–659.
"Iontophoresis", excerpt from an article in The Journal of the New York State Society of Physiotherapists, Inc., Annual Issue, Jun. 1959.
Brochure–"Iontophoresis, The Non–Invasive Administration of Drugs", by Motion Control, Inc., Feb. 1979.
Brochure–"Phoresor TM Iontophoretic Drug Delivery System Instructions", by Motion Control, Inc.
ALZA Corporation report to Shareholders, Undated.
Brochure of Medco Products, Co., Inc., Jun. 1979.
Paper Entitled "D.C. (Galvanic) Current", Unidentified as to Source and Date.
Paper Entitled, "Electro Diagnosis", Dated 8-12-71, by Medco Products, Co., Inc.
Article Entitled, "A new Screening Test for Cystic Fibrosis", from Pediatrics, vol. 36, No. 5, Nov. 1965.
Saltesmo Paper Brochure, (Undated).
Article Entitled, "An Improved Adhesive Patch for Long-Term Collection of Sweat", Biomat., Med. Dev., Art. Org., 8(1), 13–21, (1980).

Primary Examiner—Lee S. Cohen
Assistant Examiner—Angela D. Sykes
Attorney, Agent, or Firm—Schroeder, Siegfried, Vidas & Arrett

[57] ABSTRACT

This invention provides a method for performing a simple "sweat test" with particular use in screen testing for cystic fibrosis. The method includes the use of an iontophoretic device adapted for ambulatory use which has a self-adhesive drug-impregnated electrode for the stimulation of sweat coupled with the subsequent use of a test patch device for performing the analysis of the sweat in situ. For cystic fibrosis diagnosis, the test patch is particularly adapted to determine chloride concentration in the sweat when the concentration exceeds a predetermined level.

3 Claims, 10 Drawing Figures

NON-INVASIVE DIAGNOSIS METHOD

DESCRIPTION

Background of the Invention

Generally, this invention relates to a method involving the use of an ambulatory iontophoretic device on a subject to generate sweat followed by the use of a test patch in situ for reacting with the sweat to provide diagnostic information visually as by color change or the like.

The invention specifically relates to a simple "sweat test" for the diagnosis of cystic fibrosis, particularly for massive screening of subjects. In its preferred embodiment, this invention relates to a method for accomplishing this purpose wherein an ambulatory iontophoretic device is utilized for the stimulation of sweat and an absorbent quantitative test patch device is utilized to perform the analysis of the sweat in situ for chloride concentration determination within a range indicative of the presence of cystic fibrosis.

It is well documented in the literature that cystic fibrosis patients have an abnormally high chloride ion concentration present in their sweat. Typical diagnostic concentration levels indicate that most cystic fibrosis patients have greater than 30 mM of sweat chloride and most normals have below 50 mM with very little overlap in the 30–50 region.

The standard "Gibson & Cook" sweat test is well known for use in the diagnosis of cystic fibrosis. The technique uses pilocarpine nitrate iontophoresis for sweat production and laboratory analysis of the sweat for chloride concentration using a chloridometer. Existing acceptable techniques for completing "sweat tests" require skilled personnel to perform laboratory analysis of collected sweat samples. Such techniques are, therefore, costly and are not acceptable for massive screening tests.

BRIEF SUMMARY OF THE INVENTION

This invention provides a simplified procedure for the generation of sweat and the in situ diagnosis of the contents thereof for various purposes with apparatus that can be utilized by non-technical personnel. The invention makes use of a simple, compact, self-contained sweat stimulator which uses self-adhesive drug-impregnated electrodes and the application of a test patch device which provides in situ visual indication of sweat content, an indication of above normal concentrations of chloride in the sweat for cystic fibrosis screen testing. The invention will hereinafter be described with particular reference to cystic fibrosis diagnosis or screen testing. However, it is to be understood that it is applicable to any situation in which a test patch is to be used to react with any sweat component or components to provide a visual indication thereof for diagnostic purposes.

Specifically, the invention provides for the use of the self-contained iontophoretic sweat stimulator device to introduce an ionic substance such as pilocarpine into body tissue. The device comprises a casing containing an electric current source, a first electrode plate means mounted on the casing for receiving a first electrode element and for electrically coupling the first electrode element to the current source. A second electrode means is mounted on the case and coupled to the current source. Preferably, the second electrode means is also a plate means for receiving a second electrode element and the plates are composed of stainless steel. The casing and plate combination forms an integral unit that can survive considerable abuse and requires little care. The device is utilized by applying adhesive, drug-impregnated electrode pads to the metal plates and then applying the entire unit to the body in a manner similar to the application of a self-adhesive bandage. Thus, this iontophoretic device lends itself to rapid use and reuse and to ambulatory therapeutic and diagnostic uses.

A safety strap may be fixed to the casing for further securing the device to the body. The safety strap is particularly useful when the electronics of the current source are relatively bulky. However, as the electronics are reduced, as for example with microelectronic circuits and power sources, the safety strap may be eliminated.

As is known in the art, pilocarpine nitrate stimulates localized sweat formation in a subject to which it has been applied iontophoretically. After the pilocarpine has been administered, the sweat stimulator is removed. The stimulation site may then be washed with distilled water. A test patch device is then applied to the skin to react with the sweat.

The preferred test patch device for diagnosing cystic fibrosis includes a first reaction area in the form of a circular absorbent body contacted by a surrounding flat ring-shaped body of absorbent material which provides a second reaction area. The outer or perimeter edge of the circular first reaction area contacts the inner edge of the ring-like second reaction area. A third reaction area in the shape of a small absorbent indicator tab contacts the outer edge of the second reaction area body. The indicator purpose of the tab is to signify when the device is saturated with a given volume of sweat. The preferred test patch is more fully described in copending application entitled "FLUID ABSORBENT QUANTITATIVE TEST DEVICE", filed of even date herewith, the subject matter of which is incorporated herein by reference.

The absorbent bodies are enclosed in a flat fluid-tight envelope which is transparent on at least the top side for visibility of the absorbent bodies. The opposite side contains an inlet opening aligned with the center of the first reaction area for the introduction of sweat thereto. This side also carries a fluid collector designed to direct sweat to the inlet opening.

By selecting absorbent bodies of known absorbency and sizing them properly, the test patch device is constructed and arranged to absorb a predetermined fixed volume of sweat to be quantitatively evaluated for chloride concentration in excess of a predetermined level.

The inner circle or first reaction area is impregnated with a predetermined amount of reactant which is provided in an amount sufficient to react with all of the chloride contained in the absorbed sweat below a predetermined concentration, such as 50 mM.

The second reaction area or outer ring is also impregnated with a reactant which reacts with chloride in the sweat. However, since the sweat is introduced at the center of the first reaction area which is circular and must migrate radially therethrough before reaching the surrounding second reaction area, the composition in the first reaction area reacts with the chloride content in the sweat below the predetermined value first. Any chloride in the sweat in excess of the predetermined value is free to react with the reactant in the second reaction area only upon migration of the fluid thereto.

The reactant in the second reaction area is selected to provide a color change upon exposure to or reaction with the excess chloride thereby visually indicating the fact that chloride in excess of the predetermined concentration is present in the sweat.

The fill indicator tabs contain a reactant sensitive to sweat or some component therein and undergoes a visual change in appearance upon being contacted by the migrating sweat to indicate that the first and second reaction areas are saturated with the sweat and a fixed volume thereof has, therefore, been collected. This signifies completion of an individual test.

Other types of test devices may be used as long as they are adapted to produce a visual indication eg., color change or the like, for determination of the desired test results.

Numerous other features, objects and advantages of the invention will become apparent from the following detailed description when read in conjunction with the accompanying drawing.

DESCRIPTION OF THE PREFERRED EMBODIMENT

The invention includes the application of an iontophoretic device particularly adapted for ambulatory use which has self-adhesive drug impregnated electrodes for application to the skin of a subject. The device is electrically activated to drive pilocarpine nitrate from the drug impregnated electrode through the skin into the body of the subject. The pilocarpine induces the body to sweat in the localized area where the drug is applied. The second major step of the invention comprises the application of a test patch device to the skin area of the subject where the sweat forms and reading the test patch to determine if cystic fibrosis is indicated.

The compact portable apparatus and the simplified method allow for the convenient use of the method with children, particularly for performing screening tests for cystic fibrosis.

Figures 1, 2A, 2B, 3:
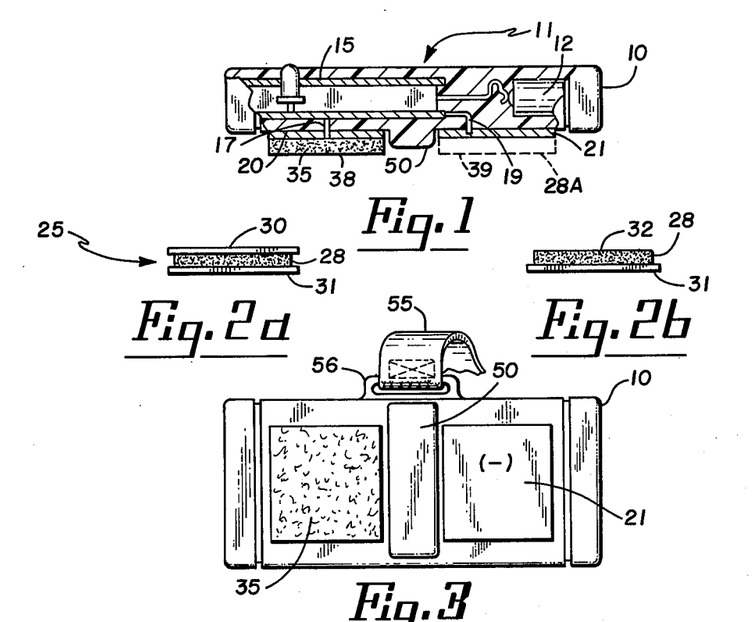
FIG. 1 is a partially cut away side view of a preferred embodiment of a compact iontophoretic device for ambulatory use according to the invention showing one adhesive electrode pad in place on the device.
FIG. 2a is an end view of an adhesive electrode as it may be manufactured and sold.
FIG. 2b shows the electrode pad of FIG. 2a just prior to its application to a preferred embodiment of the invention.
FIG. 3 is a bottom view of the device of FIG. 1.

A cut away view of an exemplary embodiment of a preferred iontophoretic device for use with the invention is shown in FIG. 1. Casing 10 contains electric current source 11 which includes a battery power source 12 and an electronics package 15. The electric current source 11 is coupled via leads 17 and 19 to electrode plate means 20 and 21, respectively.

The embodiment shown in FIG. 1 may be prepared for use by applying electrode elements, such as shown in FIGS. 2a and 2b to electrode plates 20 and 21. The electrode 25 comprises a sheet-like adhesive pad 28 having protective backing sheets 30 and 31 covering its broad surfaces as shown in FIG. 2a. In FIG. 2b the protective sheet 30 has been removed exposing the adhesive surface 32. The pad 28 may be then applied to one of the electrode plates of the device such as 21. In FIG. 1 the pad is shown in ghost at 28a in the position it would occupy when applied to plate 21. The entire device may then be applied to the body of a test subject.

Adhesive pads such as 35 and 28 are composed of pilocarpine nitrate admixed with an adhesive. When the device of FIG. 1 is applied on the body with the lower surfaces such as 38 of the pads against the body and the device is turned on, the pilocarpine nitrate in the pad is driven into the body. For example, a pad containing the pilocarpine nitrate is placed on the positive electrode plate 20 and an indifferent electrode pad in which the ionic substance may be a salt such as potassium sulfate, which has ions of both positive and negative polarity, may be placed on the negative electrode. The electrode pads such as 28 and 35 and the backing sheets, such as 30 and 31, may be color-coded for identification and/or may be marked with positive or negative symbols to clearly identify which of plates 20 and 21 they should be applied to. The adhesive pads such as 28 and 35 are more fully discussed in U.S. patent application Ser. No. 241,150, filed Mar. 6, 1981, a companion application to the present application. Additionally, U.S. patent application Ser. No. 240,740, filed Mar. 5, 1981 and U.S. patent application Ser. No. 241,284, filed Mar. 6, 1981 now U.S. Pat. No. 4,406,658 issued Sept. 27, 1983 describe further details regarding iontophoretic devices useful in this invention. The content of these applications is hereby incorporated by reference.

Turning attention to FIG. 3 a bottom view of the preferred sweat stimulator device according to the invention is shown. It is seen that in this embodiment the plates 20 (shown covered with pad 35 in FIG. 3) and 21 are of generally square shape, although any shape may be chosen. A negative sign may be placed on plate 21 as shown. A positive sign may be carried by plate 20 (not shown) which is covered by pad 35. Plates 20 and 21 are separated by a raised ridge 50, portion of housing 10, which ridge 50 ensures the electrical separation of pads 35 and 28a. As can be seen in FIG. 1, ridge 50 extends below the surface of plates 20 and 21 but does not extend as far as the surfaces 38 and 39 of pads 35 and 28a. Should the iontophoretic device be attached to a limb or other portion of the body with such force that pads 35 and 28 become displaced in a horizontal direction from their correct position, ridge 50 prevents their physical contact which would short out the iontophoretic circuit. Ridge 50 also assists in the rapid application of pads such as 35 and 28a to plates 20 and 21.

Strap 55 is provided to assist in holding device 11 to the body to which the device is applied. Strap 55 is attached to strap anchor 56 on housing 10. In the embodiment shown, strap 55 is a material which adheres to itself, such as VELCRO, a Trademark of Smalley and Bates, Inc. It attaches to itself after circling the limb or other body portion, and thus only one strap anchor 56 is necessary. Strap 55 is provided because in the embodiment shown, housing 10, battery 12 and electronics 15 have sufficient mass so that the device might become separated from the body during rapid movements of the limb or other body portion to which it is applied. The invention contemplates that circuitry 15 and power source 12 may be made extremely small and of relatively low mass using state of the art technology, in which case strap 55 may be eliminated.

Figure 4:
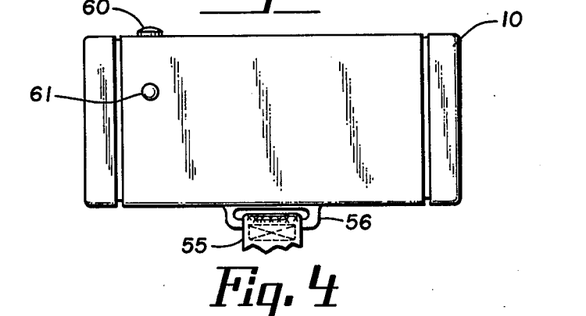
FIG. 4 is a top view of the device of FIG. 1.

As shown in FIG. 4, OFF/ON switch 60 and light-emitting diode (L.E.D.) 61 protrude through housing 10. Switch 60 is used to activate the iontophoretic device. Diode 61 serves to indicate whether the current is on or off and provides battery life indication. These shall be discussed below in more detail in connection with the electronic circuitry.

Figure 5:
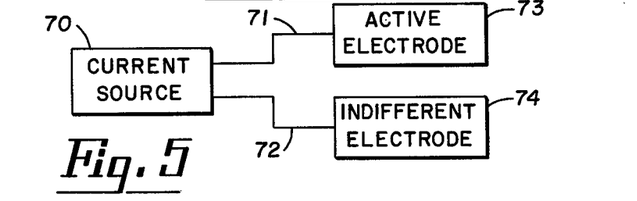
FIG. 5 is a block diagrammatic illustration of circuitry for an iontophoretic device.

Turning to FIG. 5 there is shown a block diagrammatic illustration of the iontophoretic circuit. This circuit includes current source 70 which is electrically coupled through coupling means 71 and 72 to electrodes 73 and 74. For purposes of illustration, electrode 73 is labeled the active electrode while electrode 74 is labeled the indifferent electrode, although the positions could be reversed. Coupling means 71 and 72 may be wires or any other means for electrically coupling the current source and the electrodes.

Figure 6:
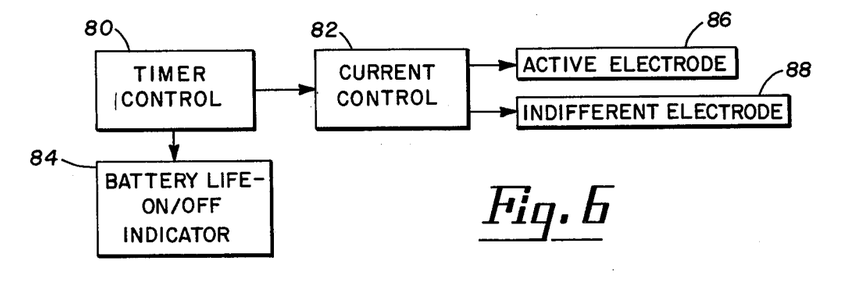
FIG. 6 is a block diagrammatic illustration of the preferred electronic circuitry for producing the iontophoretic current.

FIG. 6 shows a more detailed block diagrammatic illustration of the electrical circuit employed in the embodiment of the invention disclosed in FIGS. 1-4. Turning the switch 60 (not shown in FIG. 6) "on" activates Timer Control Circuit 80. Timer Control Circuit 80 provides a signal to Battery Life-ON/OFF Indicator Circuit 84 which, in turn, activates light-emitting diode 61 provided that the battery voltage is above a predetermined level which is considered to be sufficient to reliably operate the device. Timer Control Circuit 80 also provides a signal to Current Control Circuit 82. Current Control Circuit 82 responds to a signal from Timer Control Circuit 80 to ramp/on the iontophoretic current; that is, the iontophoretic current is turned on gradually from 0 value up to the full current value. This prevents burning, shocking or other unpleasant sensations when the current is turned on. The iontophoretic current is applied from Current Control Circuit 82 to electrodes 86 and 88. In the embodiment shown the current is such that it flows from active electrode 86 through the body to indifferent electrode 88; in other embodiments the electrodes or the direction of the current may be reversed.

The dosage of ionic substance which is applied to the body is controlled by Timer Control Circuit 80 and Current Control Circuit 82. Current Control Circuit 82 provides a constant current output to the electrode which is, within impedance range and as limited by supply voltage, independent of the load between electrodes 86 and 88, which is generally the skin impedance. Thus, the amount of ionic substance driven into the body by the current will be constant in time. In this manner control of the time over which the current is applied controls the dosage. After a predetermined amount of time Timer Control Circuit 80 applies a second signal to Current Control Circuit 82 which causes Current Control Circuit 82 to ramp the iontophoretic current off. At the same time a second signal is passed through Battery Life-ON/OFF Indicator Circuit 84 which causes the circuit to turn L.E.D. 61 "off".

Exemplary electronics for the circuit of FIG. 6 are shown in detail in the aforementioned companion application Ser. No. 240,740, filed Mar. 5, 1981.

The following example is illustrative of a process used to prepare a pilocarpine nitrate impregnated electrode for use with the iontophoretic device described herein.

EXAMPLE I 11.3 grams of pilocarpine nitrate were dissolved in 270 ml of deionized water in a 1 liter flask. To the former solution 300 grams of glycerine followed by 300 grams of polybutene were added. Next, a previously mixed combination of 225 grams of gelatin and 37.5 grams of polyvinyl pyrolidone was added. The resulting layers of components were stirred until the mixture thickened and was difficult to stir (about 2-3 minutes). A water bath heated the mix for about one hour at which time the temperature was approximately 65° C., and the mix was again fluid. The fluid mix, with continued heating, was stirred five minutes or longer to insure homogeneity, at which point the temperature was approximately 75° C. The composite was poured into a polyethylene plastic pan, covered with aluminum foil and refrigerated until set.

About 3 hours later the composite was weighed into approximately 100 gram amounts. These were placed within a $6\frac{1}{2}"\times6\frac{1}{2}"\times\frac{1}{8}"$ brass frame between sheets of Mylar. The sandwiched composite was placed between the platens of a compression molder at about 55° C. and subjected to 20,000 lb. ram force for 2 to 3 minutes.

The sheet of pressed composite was cut with a stainless steel scalpel into squares $1\frac{1}{8}"\times1\frac{1}{8}"$ while still between Mylar. The electrodes formed in this manner were applied to electrode plates 20 and 21 of an iontophoretic generator such as shown in FIGS. 1 and 3, as previously described, with relative ease. After the iontophoretic process described above was completed it was found that there was good uniform pilocarpine introduction into the body under the entire pad with minimal hot spots and burning.

As has already been pointed out, the mixture of pilocarpine nitrate and an adhesive material is applied to the skin of a test subject. By using the iontophoretic device described herein, an electrical current is driven through the mixture to drive the pilocarpine nitrate into the body. The body is then allowed to sweat and the sweat is analyzed as described hereinbelow, as in the case of the preferred embodiment, for its chloride content to determine the presence of cystic fibrosis. The use of the above described device permits precise control of the pilocarpine nitrate introduced into the body. At the same time, it substantially simplifies the medical procedures necessary to introduce the pilocarpine nitrate, thus making it much more practical to use the diagnostic method as a means of screening large numbers of persons, such as all new born infants, for cystic fibrosis. The more controlled and easier application also results in the iontophoretic method being much more practical than heretofore.

The analysis of the sweat formed by the application of the pilocarpine nitrate is preferably by means of the aforementioned test patch device, as exemplary type of which will now be described in detail. Any other in situ test device may be utilized which provides a visual analytical indication.

The particular, preferred quantitative test patch device described herein is intended for use in the second step of screen testing subjects for cystic fibrosis. Any in situ testing means, particularly a test patch, preferably self-adhesive, capable of reacting with sweat or a component thereof to provide visual analytical indication for diagnostic purposes is contemplated as being within the purview of this invention.

The particular test patch described herein is preferably constructed and arranged to absorb about a 50 μl test sample of sweat and to indicate the presence of chloride in sweat in excess of a predetermined level of about 45 mM by providing a suitable color change in the outer ring of the device i.e., a colormetric response. It may be modified to absorb differing amounts of sweat as desired and to provide visual indication of various amounts of chloride as desired. The specific construction of this test patch does not form a part of the present invention per se.

Figure 7:
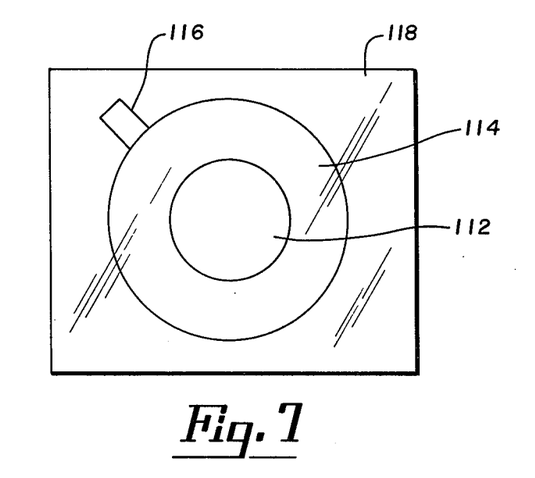
FIGS. 7 and 8 are top and bottom views, respectively, of a test patch device for use with the invention.
Figure 8:
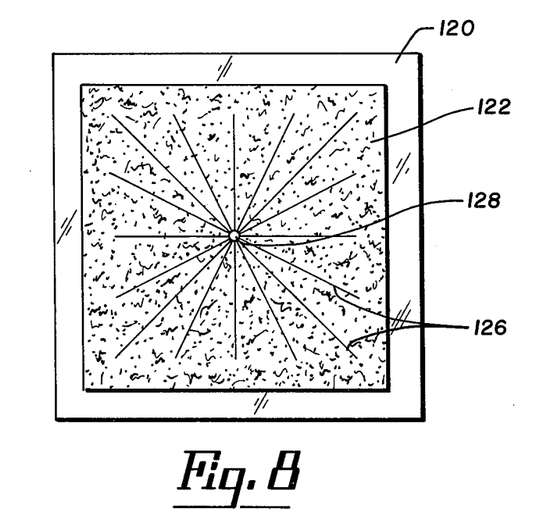
Figure 9:
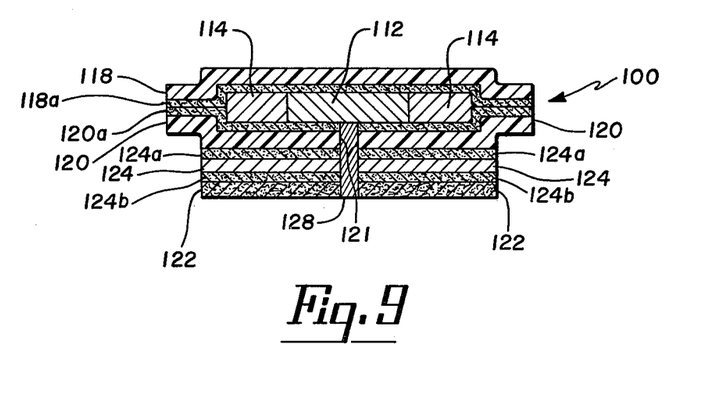
FIG. 9 is a schematic cross section taken through the center of the device of FIG. 7.

Referring now to FIGS. 7–9, a preferred quantitative test device for cystic fibrosis screening is comprised of an indicating layer generally indicated at 100 in FIG. 9. Indicating layer 100 includes inner circle 112, concentric ring 114 and indicator tab 116 (best seen in FIG. 1). Circle 112, ring 114 and tab 116 are of absorbent material such as filter paper or chromatography paper and are preferably substantially flat. These bodies are assembled such that circle 112 lies inside ring 114 with the outer edge of circle 112 contacting the inner diameter of ring 114. Tab 116 contacts the outer diameter or edge of ring 114 as shown. Upon assembly of the three absorbent bodies into their operating relationship they may be subjected to pressure eg., 2600 lbs/sq inch to press them together. Tab 116 may be modified into various other shapes. For example, it may be a third concentric ring or ring segment. Generally it may be any shape or form so long as it contacts the outer edge of ring 114 and provides a visual color change when contacted by the fluid being absorbed.

The arrangement shown provides an indicating layer capable of absorbing a given volume of sweat depending on the size and weight of the absorbent paper selected and the overall size of the circular and ring-shaped bodies.

Indicating layer 100 is enclosed in a non-absorbent fluid-tight envelope comprised of an overlaying transparent layer 118 and an underlying backing layer 120. Layer 120 may be transparent also but not necessarily. A suitable and most preferred material for layers 118 and 120 are adhesive plastic tape such as polyester tape obtained from Bel-Art Products, Pequannock, N.J. which markets the tape identified as "Lab Label Protection Tape". This tape carries an adhesive on one surface as shown at 118a and 120a and has been found to be somewhat resistant to cold flow, non-absorbent and suitably transparent for use in forming the envelope in which indicating layer 100 is sealed between the opposing adhesive surfaces of the tape as shown. Layer 120 is then provided with a small central opening 121 aligned with the center of circle 112 to provide an inlet opening for sweat to gain access to indicating layer 100.

A sweat collector 122, preferably comprised of high density polyethylene non-woven sheet such as TYVEK ®, a trademark of the Paper Manufacturing Company of Philadelphia is then attached to layer 120. Preferably, this is accomplished by means of a double backed adhesive (124a and 124b) plastic tape 124 such as Tape No. 1512 available from the 3M Company of St. Paul, Minn. Sweat collector 122 and plastic tape 124 also contain a central inlet opening aligned with the opening in layer 120 and with the center of circle 112. A piece of absorbent paper 128 or the like is inserted into the inlet opening of the sweat collector as a wick-like plug through which sweat enters the device to gain access to indicating layer 100. Sweat collector 122 also includes a plurality of radiating indentations 126 (best seen in FIG. 8) which function to channel sweat to the inlet opening. These indentations may be formed by pressing or scribing the contact surface of the collector, i.e., the surface which is intended to contact the skin.

Inner circle 112 of indicating layer 100 is impregnated with a reactant so as to screen out all chloride in the sweat absorbed by the indicating layer below a predetermined concentration such as the aforementioned 45 mM. Outer ring 114 of indicating layer 100 is impregnated with a reactant so as to reflect the presence of chloride in excess of the screened concentration level by undergoing a color change to visually indicate the presence of the excess chloride. Tab 116 is also impregnated with a suitable composition to provide a visual indication that the indicating layer is saturated with the intended volume of sweat such as the aforementioned 50 μl amount. The fill indicator tab 116 undergoes a color change only if the device absorbs the required volume of sweat. This serves as an indication that insufficient sweat has been generated and absorbed and likewise as an indicator that a sufficient amount of sweat has been generated and absorbed to complete the test.

The preferred absorbent medium for bodies 112, 114 and 116 is filter paper or chromatography paper. No. 20 chromotography paper from Whatman, Inc., Paper Division, Clifton, N.J. is most preferred.

Circles of desired size for inner circle 112 are cut from sheets of such paper which have been impregnated with a controlled amount of silver phosphate. Preferably, the sheet is first impregnated with silver nitrate and dried. It is then impregnated with sodium phosphate to cause the formation of silver phosphate precipitate in situ. These operations must be performed in subdued light. The silver phosphate thus formed has been found to be relatively immobile in the paper thus remaining fixed when the sweat migrates through the circle. It gives the paper a yellow appearance.

Indicating rings 114 are also cut to desired size from sheets of No. 20 chromatography paper which have been impregnated with silver chromate. The impregnation process is analogous to that described above in that the paper is first wetted with a silver nitrate solution, dried and then wetted with a potassium chromate solution forming silver chromate in situ.

Fill indicator tabs 116 are cut from sheets of paper which have been impregnated with silver nitrate.

Circle 112 (silver phosphate paper) is fitted inside brown ring 114 (silver chromate paper) and pressed together at 2600 lbs/sq. inch. This assembly is then placed on the adhesive side 118a of non-absorbent tape 118. Fill indicator tab 116 is placed on adhesive side 118a of tape 118 so that one edge touches the outer edge of ring 114. A hole or inlet opening, preferably about 0.04 inches, is punched in a second piece of tape i.e., layer 120 and this tape is placed over the paper bodies which are then sealed between the two tape layers with gentle pressing. The hole therein should be aligned so that it is in the center of circle 112. Channels 126 are formed in a radiating pattern in collector 122 which is preferably a piece of high density polyethylene non-woven fiber sheet. A hole, approximately about 0.04 inches preferably, is punched in the center of sheet 122 and the sheet is attached to tape layer 120, with the holes aligned, by means of the non-absorbent double-backed adhesive tape 124 which also has an 0.4 inch hole in its center. A plain piece of No. 20 chromatography paper is punched and fit into the hole in the polyethylene sheet 122 as indicated at 128.

Sweating is induced by use of the aforementioned iontophoretic device. After the skin has been cleaned, the test device is then taped over the clean area with the collector side next to the skin. As sweat is generated, the collector directs it to the inlet opening where it enters the device by passing through the wick-like plug. The sweat enters the device to be absorbed at the center of inner circle 112. It radially diffuses through this first reaction area. Chloride in the diffusing sweat reacts with the impregnated silver phosphate in circle 112 as shown in reaction (1).

(1) $2H_2O + 3Cl^- + Ag_3PO_4 \rightarrow 3AgCl + H_2PO_4^{--} + 2OH^-$

As already indicated, sufficient silver phosphate has been impregnated in circle 112 so as to complex all chloride in the absorbed sweat sample below a predetermined concentration such as the aforementioned 45 mM value.

The sweat sample continues to radially diffuse outwardly and it enters ring 114. Any excess chloride i.e., chloride not reacted with the silver phosphate in circle 112, then reacts with the impregnated silver chromate in ring 114 as shown in reaction (2).

(2) $2Cl^- + Ag_2CrO_4 \longrightarrow AgCl + CrO_4^=$
  (Brown)      (White)

Consequently, any chloride above the predetermined concentration is indicated visually by the appearance of a white area in ring 114.

Ring 114 preferably contains silver chromate formed in situ plus a slight excess amount of potassium chromate such as is indicated in Example II below. As the sweat sample continues to diffuse outwardly in ring 114 it carries some of the soluble potassium chromate with it. When fill indicator tab 116 is contacted by the sweat sample now containing the soluble chromate the reaction takes place shown at (3).

(3) $2AgNO_3 + CrO_4^= \longrightarrow Ag_2CrO_4 + 2NO_3^-$
  (Brown)

The tab turning brown indicates that sufficient sweat has been collected to saturate indicating layer 100 and that the test is complete.

EXAMPLE II

A test patch capable of holding a 50 μl sweat sample and producing a color change in the indicating layer at 45 mM level of chloride concentration should have the following characteristics:

(1) inner circle 112—½ inch diameter impregnated with $1.7 \times 10^{-6}$ moles of silver phosphate (2) indicating ring 114—1 inch OD/one half inch ID, impregnated with about $2.2 \times 10^{-6}$ moles of silver chormate and $4 \times 10^{-7}$ moles of potassium chromate. The excess chromate is used to produce the color change in fill tab 116 when the device is completely filled with fluid.

(3) fill indicator 116—⅛ inch×¼ inch impregnated with $1.2 \times 10^{-7}$ moles of silver nitrate. (Paper used throughout—Whatman No. 20 chromatography grade, thickness 0.165)

The amount of silver in circle 112 is slightly less than the amount required to complex all of the chloride in 50 μl of a 45 mM sample. The reason for this is that the last of the sweat sample to enter the test patch at inner circle 112 does not diffuse out to ring 114 and is therefore not involved in the reaction.

Silver dichromate may also be used as the screening composition in ring 114. Cuprous chloride and chromic chloride may be used as color indicators for fill tab 116.

The following procedure has been found to be useful in impregnating the paper with a reproducible and evenly distributed amount of reactant.

A piece of dry bulk paper of known weight and size is saturated with water, placed between two sheets of 5 mil plastic sheet eg., Teflon and passed through the rollers of a pasta maker to remove excess water. The bulk paper is immediately reweighed and from the difference in weight (wet-dry) the impregnation volume can be calculated. Using a #1 setting on the pasta maker, the procedure yielded an average impregnation amount of 39 μl/in²±1 μl/in². It was noted that the speed one uses in rotating the rollers has an effect on impregnation amounts. If the speed is slow more liquid is squeezed out of the paper. If it is fast, less liquid is squeezed out and the resulting impregnation volume is higher. Uniform speed is therefore desired throughout.

Once the impregnation volume of the paper is determined, the concentration of the various impregnation solutions can be determined for any given situation.

Two important volumes must be known in order to construct this test patch. The first is the impregnation volume of the paper. This is a volume of impregnation solutions per square inch that the paper will hold. It must be experimentally determined using whatever impregnation procedure is developed, such as the method using pasta rollers described above. For Whatman #20 paper the impregnation volume was found to be 39±1 μl per square inch under the condition described here. Once this volume is known the concentration of chemicals needed to impregnate the bulk paper can easily be determined.

The second volume of interest is the volume the test patch will absorb during the screening test. It should be noted that this volume may be quite different from the impregnation volume. The absorption volume must be determined for the patch as constructed, i.e., with the specific kind of paper and the pressing conditions used during construction. For the test patch of the preferred embodiment the absorption volume was found to be 64±3 μl per square inch. It must be remembered that a volume of solution equal to that absorbed by inner circle 112 will never migrate to the outer ring 114 during the test. Therefore, the calculation of the amount of silver phosphate needed to be impregnated into inner circle 112 depends only upon the size of outer ring 114. Therefore, the volume of impregnation chemicals are calculated from the absorption volume and the size of the outer ring. It turns out that $1.7 \times 10^{-6}$ moles of chloride must be screened out in inner ½ inch circle 112 in the preferred embodiment. The impregnation volume for a ½ inch diameter circle is equal to 39 μl/sq. in×0.20 sq. in. (circle area) or 7.8 μl. This volume of solution must contain the required amount of silver for screening out the chlordie or $1.7 \times 10^{-6}$ moles. The concentration of the $AgNO_3$ impregnating solution is therefore $1.7 \times 10^{-6}$ moles divided by 7.8 μl or 0.22M. The $AgNO_3$ is reacted with $Na_2HPO_4$ to provide the fixed silver phosphate reactant. A 0.21M $AgNO_3$ solution requires a 0.07M $Na_2HPO_4$ solution for stoichiometric formation of silver phosphate.

The preferred embodiment of the invention uses a test patch including an inner circle 112 of ½ inch diameter and an outer ring 114 about it bringing the total area to one square inch. The inner circle 112 must be impregnated with a specific amount of a certain concentration of $AgNO_3$. This is necessary so that the $AG_3PO_4$ can be formed in the inner circle 112 in a predetermined amount which will screen out 45 mM of chloride (or whatever predetermined amount is desired) in a given volume of sweat, such as 50 μl. The outer ring 114 is the indicating area for any excess chloride. Thus, the need for a calculated impregnation amount of reactant in that reaction area is also important.

Outer ring 114 is used only as an indicating layer for excess chloride and the specific concentration of $Ag_2CrO_4$ is not critical. However, it has been determined that lower concentrations of $Ag_2CrO_4$ produce a more desirable result due to the fact that any excess chloride will produce a more significant visual change. Specifically, if one uses a high concentration of $Ag_2CrO_4$, when the excess chloride enters the outer ring 114 there is so much silver ion in close proximity to the inner circle 112 that all AgCl formation occurs in the area of the outer ring which is in very close proximity of the inner circle. By lowering the silver chromate concentration somewhat in the outer ring, the chloride can migrate further into it to provide an enlarged area of reaction and hence an enlarged visual indication of excess chloride. For example, one may preferably use 0.10M $AgNO_3$ and 0.07M $K_2CrO_4$ solution to impregnate outer ring 114 for the preferred embodiment of the invention.

The embodiment described herein has been by way of illustration only.

Having considered the above description, it will be appreciated that the method of the invention includes the steps of: applying a self-contained iontophoretic device for ambulatory use, the device having a self-adhesive drug-impregnated positive electrode, to the body of a subject; turning the device "on" to drive the drug into the body by iontophoretic action thereby inducing localized sweat formation, and applying a test patch or other in situ indicator to the body to contact the sweat (preferably at the location where the drug was applied), the test patch or other device being particularly adapted to provide visual indication of a predetermined characteristic of the sweat.

What is claimed is:

1. A method of non-invasive diagnosis comprising the steps:

contacting the skin of a subject with an adhesive, iontophoretic, sweat-inducing drug-impregnated electrode carried by a self-contained iontophoretic device particularly adapted for ambulatory use whereby the device may be secured to the body of the subject;

activating the device while so secured to drive the drug from the electrode into the skin of the subject whereby sweat formation is induced on the skin;

removing the device from the body, and collecting a predetermined volume of the sweat in situ with an absorbent test device constructed and arranged to provide a visual analytical quantitative indication of a predetermined component of the sweat in excess of a predetermined amount, the test device including an outer fluid-tight envelope with a transparent viewing portion and an inlet for the entrance of sweat thereto.

2. The method of claim 1 wherein the test device is constructed and arranged to collect a predetermined volume of sweat on a centrally located circular sweat-collecting absorbent medium which contains a substance for reacting with amounts of the predetermined component of the sweat below a predetermined concentration thereof and a surrounding absorbent medium contains a substance which reacts with amounts of the predetermined component of the sweat in excess of the predetermined amount reaching it to provide a visual indication of amounts of the component in the sweat in excess of the predetermined concentration.

3. The method of claim 2 for cystic fibrosis diagnosis wherein the in situ analysis is directed to the determination of chloride concentration in the sweat.

* * * * *

UNITED STATES PATENT AND TRADEMARK OFFICE
CERTIFICATE OF CORRECTION

PATENT NO. : 4,457,748
DATED : July 3, 1984
INVENTOR(S) : Gary A. Lattin et al

It is certified that error appears in the above-identified patent and that said Letters Patent are hereby corrected as shown below:

Column 2, line 33, the phrase "indicator purpose of the tab" should read --purpose of the indicator tab--.

Signed and Sealed this

Twenty-third Day of October 1984

[SEAL]

Attest:

GERALD J. MOSSINGHOFF

Attesting Officer

Commissioner of Patents and Trademarks

UNITED STATES PATENT AND TRADEMARK OFFICE
CERTIFICATE OF CORRECTION

PATENT NO. : 4,457,748

DATED : July 3, 1984

INVENTOR(S) : Gary A. Lattin and Richard P. Spevak

It is certified that error appears in the above-identified patent and that said Letters Patent are hereby corrected as shown below:

On the cover page of the patent, first column, after "Inventors:", line 2 thereof, the inventor's name spelled as "Spevar" should read --Spevak--.

Signed and Sealed this

Nineteenth Day of March 1985

[SEAL]

Attest:

DONALD J. QUIGG

Attesting Officer  Acting Commissioner of Patents and Trademarks